(12) United States Patent
Gupta et al.

(10) Patent No.: US 9,714,322 B2
(45) Date of Patent: Jul. 25, 2017

(54) TRIFUNCTIONAL BENZOXAZINE

(71) Applicant: Cytec Industries Inc., Woodland Park, NJ (US)

(72) Inventors: Ram B Gupta, Stamford, CT (US); Paul Mark Cross, York (GB)

(73) Assignee: Cytec Industries Inc., Woodland Park, NJ (US)

( * ) Notice: Subject to any disclaimer, the term of this patent is extended or adjusted under 35 U.S.C. 154(b) by 0 days.

(21) Appl. No.: 14/980,407

(22) Filed: Dec. 28, 2015

(65) Prior Publication Data
US 2016/0185907 A1    Jun. 30, 2016

Related U.S. Application Data

(60) Provisional application No. 62/097,276, filed on Dec. 29, 2014.

(51) Int. Cl.
| | | |
|---|---|---|
| C08G 63/02 | (2006.01) | |
| C08G 73/02 | (2006.01) | |
| C07D 265/16 | (2006.01) | |
| C08J 5/24 | (2006.01) | |
| C08L 79/02 | (2006.01) | |

(52) U.S. Cl.
CPC ........ *C08G 73/0233* (2013.01); *C07D 265/16* (2013.01); *C08J 5/24* (2013.01); *C08L 79/02* (2013.01); *C08J 2379/02* (2013.01)

(58) Field of Classification Search
CPC .......................... C08G 73/0233; C07D 265/16
USPC ....................................................... 528/212
See application file for complete search history.

(56) References Cited

U.S. PATENT DOCUMENTS

| | | |
|---|---|---|
| 6,160,079 A | 12/2000 | Ishida et al. |
| 7,781,561 B2 | 8/2010 | Lin et al. |
| 8,148,028 B2 | 4/2012 | Choi et al. |
| 8,426,081 B2 | 4/2013 | Choi et al. |
| 2007/0184323 A1 | 8/2007 | Lee et al. |
| 2009/0270615 A1 | 10/2009 | Taden et al. |
| 2015/0175746 A1* | 6/2015 | Ward .................. C08G 73/0233 428/221 |

FOREIGN PATENT DOCUMENTS

| | | |
|---|---|---|
| CN | 103387791 A | 11/2013 |
| WO | 03072638 A1 | 9/2003 |
| WO | 2013148408 A1 | 10/2013 |

OTHER PUBLICATIONS

International Search Report. PCT/US2015/067627. Mailing date: Mar. 22, 2016.
Choi Seong-Woo et al., "Preparation of Dendritic Macromolecules Containing Benzoxazine moiety", Polymer Preprints, American Chemical Society U.S., Jan. 1, 2001, vol. 42, No. 2.

* cited by examiner

*Primary Examiner* — Terressa Boykin
(74) *Attorney, Agent, or Firm* — Thi Dang (57) ABSTRACT

A meta-substituted trifunctional benzoxazine monomer and compositions containing the same, wherein the trifunctional benzoxazine monomer is represented by the following structure:

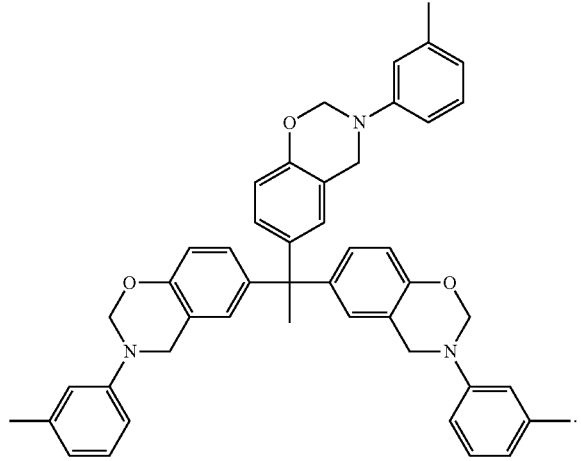

18 Claims, 5 Drawing Sheets

Post cured
230°C, 2.5 hrs

FIG.4B

TRIFUNCTIONAL BENZOXAZINE

This application claims the benefit of U.S. Provisional Patent Application No. 62/097276, filed Dec. 29, 2014, the disclosure of which is incorporated by reference in its entirety.

The use of benzoxazines (BOX) offers a number of advantages as compared to other thermosetting resins such as epoxies. Those advantages include relatively long shelf-life, molecular design flexibility, low cost, high glass transition temperature ($T_g$), high modulus, relatively low viscosities, good flame retardant properties, low moisture absorption, no by-products released during curing and very low shrinkage upon curing. Furthermore, benzoxazines are capable of being self-cured upon heating; i.e. there is no need for an additional curing agent.

DETAILED DESCRIPTION

The present disclosure pertains to a meta-substituted trifunctional benzoxazine monomer, a reaction product composition containing the meta-substituted trifunctional benzoxazine monomer as a major component, and use thereof in curable resin compositions and composite materials.

The substituted trifunctional benzoxazine monomer of the present disclosure contains three benzoxazine rings, each containing a meta-toluidine (or m-toluidine) substituent, and is represented by the following Structure I:

Tris-BOX with m-toluidine

Note that the position of the methyl group ($CH_3$) is bonded to the toluidine ring at the meta position relative to N. This benzoxazine monomer has a molecular weight (MW) of 699 as determined by Liquid Chromatography Mass Spectrometry (LCMS) using electrospray ionization technique. The chemical name of the above mentioned trifunctional benzoxazine monomer is 6,6',6''-ethane-1,1,1-triyltris (3-(3-methylphenyl)-3,4-dihydro-2H-1,3-benzoxazine (also referred herein as "m-tris benzoxazine").

The synthesis of the m-tris benzoxazine monomers may be carried out according to one of the following reaction schemes.

Scheme 1

Tris-BOX with m-toluidine-MW 699
(A)

According to Scheme 1 (shown below), the m-tris benzoxazine monomer is obtained from the reaction of trihydric (or tris-) phenol (i.e., a phenol having three reactive hydroxyl groups), preferably, 1,1,1-tris(4-hydroxyphenyl) ethane, m-toluidine, and methyl formcel.

In the reaction above, m-tris-benzoxazine, structure (A), is the major component of the reaction product composition, but there are also minor components which are represented by structures (B) and (C) below:

(B)

Minor Product: MW 687

(C)

Minor Product: MW 568

The molecular weight of structure (B) and (C) are 687 and 568, respectively, as determined by LCMS using electrospray ionization technique. In the reaction of Scheme 1, the stoichiometry of the reactants may be as follows: for each mole of m-toluidine, 0.25-0.5 of tris-phenol, and 1.5-20 moles of methyl formcel.

According to one embodiment, the benzoxazine monomers are formed by first reacting m-toluidine with methyl formcel to generate an N-methoxymethyl intermediate. Subsequently, the intermediate compound is reacted with tris-phenol to generate the benzoxazine monomers. In an alternative embodiment, the benzoxazine monomers are formed by mixing m-toluidine with tris-phenol and methyl formcel, and simultaneously reacting by heating the resulting mixture to affect a reaction.

Scheme 2

Tris-BOX with m-toluidine

According an alternative reaction Scheme 2 (shown below), the m-tris-benzoxazine monomers are obtained from the reaction of trihydric (or tris-) phenol, preferably 1,1,1-tris(4-hydroxyphenyl)ethane, m-toluidine, and paraformaldehyde (or p-formaldehyde).

In the reaction of Scheme 2, the stoichiometry of the reactants may be as follows: for each mole of tris-phenol, 2.5-3.5 moles of aromatic amine, and 5-8 moles of paraformaldehyde. The reaction mixture is heated to a temperature at which the reactants chemically react and the reaction mixture is maintained at that temperature until a benzoxazine reaction product is formed.

The m-tris-benzoxazine monomer of structure (I) is a solid at room temperature (20° C.-30° C.). It has been found that this m-tris benzoxazine monomer is more reactive (i.e., reacts at a lower temperature) as compared to a similar known compound, para-trifunctional benzoxazine or "p-tris benzoxazine" (Structure II below).

(II)

Even though the two trifunctional benzoxazines of Structures I and II are similar in structure, their properties are different. The above mentioned property of the m-tris benzoxazine monomer could lead to a lower temperature cure and/or shorter cure cycle. Such property may be advantageous in the manufacturing of aerospace composite parts because the ability of a composite part to cure at lower temperatures provides a variety of benefits. In one aspect, the tooling which is used to shape the composites, such as molds, may be formed from lower cost, low temperature materials, rather than more expensive materials capable of withstanding higher curing temperatures.

Curable Resin Compositions

Upon curing, the m-tris-benzoxazine monomers readily polymerize via ring opening polymerization. Such polymerization is usually initiated cationically (using cationic initiators) or thermally.

The m-tris-benzoxazine monomers of the present disclosure could be used in blends with other benzoxazine monomers or oligomers (mono-oxazine or multi-oxazine ring benzoxazines) or other thermosettable resins to form polymer blends with desired properties. Other thermosettable resins that could be used in a blend with the m-tris-benzoxazine monomers include: epoxy resins, bismaleimide (BMI), formaldehyde condensate resins such as formaldehyde-phenol resin, cyanate ester, unsaturated polyester, phenolic resins, and combinations thereof. Suitable epoxy resins include those derived from the mono or poly-glycidyl derivative of one or more of the group of compounds consisting of aromatic diamines, aromatic monoprimary amines, aminophenols, polyhydric phenols, polyhydric alcohols, polycarboxylic acids and the like, or a mixture thereof. Other thermosettable resins (or thermoset polymer precursors) may be useful as a processing aid for the m-tris-benzoxazine monomers which are solids at ambient temperature (20° C.-30° C.). Blends of m-tris-benzoxazine monomers and other thermosettable resins may be formulated so that the curable resin compositions have properties that are suitable for processing using standard composite fabrication techniques such as prepregging and resin infusion. Particularly suitable thermosettable resins for blending with benzoxazine monomers include epoxy, cyanate ester and phenolic resin precursor, which are low-melting solid or liquid at ambient temperature.

Alternatively, the curable composition may be a neat benzoxazine system which contains blends of different benzoxazine monomers or oligomers but is void of any other thermosettable resin(s) such as epoxy, cyanate ester, BMI and phenolics as a major component. For example, the m-tris-benzoxazine monomers disclosed herein may be blended with low-melting solid or liquid monofunctional benzoxazine monomers or difunctional benzoxazine monomers such as bisphenol A-benzoxazine.

The benzoxazine blends discussed above may be combined with additional components such as catalysts and toughening agents to form a curable composition suitable for the manufacture of resinous films (e.g. adhesive films, surfacing films) or fiber-reinforced composites (e.g. prepregs).

As used herein, a "curable composition" refers to a composition prior to full curing to form a hardened matrix resin.

The addition of catalysts to the curable resin compositions is optional, but the use of such may increase the cure rate and/or reduce the cure temperatures. Suitable catalysts for the benzoxazine-based compositions include, but are not limited to, Lewis acids such as boron trifluorodietherate ($BF_3O(Et)_2$), phosphorous pentachloride ($PCl_5$), phosphorous trichloride ($PCl_5$), phosphorus oxychloride ($POCl_3$), titanium chloride ($TiCl_4$), aluminum chloride ($AlCl_3$), antimony pentachloride ($SbCl_5$); phenols such as thiodiphenol, and 2,4-di-tert-butylphenol; methyl tosylate, methyl triflate (MeOTf), cyanate esters, 2-ethyl-4-methylimidazole (EMI); strong acids such as alkylenic acids, adipic acid, p-toluenesulfonic acid.

Toughening agents (or tougheners) may be added to produce a toughened matrix resin suitable for high-strength composites, such as those used for aerospace applications. Suitable toughening agents include, but are not limited to, thermoplastic toughening agents such as polyethersulphone (PES), co-polymer of PES and polyetherethersulphone (PEES), elastomers, including liquid rubbers having reactive groups, particulate toughening agents such as, but are not limited to, thermoplastic particles, glass beads, rubber particles, and core-shell rubber particles.

Functional additives may also be included in the curable composition to influence one or more of mechanical, rheological, electrical, optical, chemical, flame resistance and/or thermal properties of the cured or uncured resin composition. Examples of such functional additives include, but are not limited to, fillers, color pigments, rheology control agents, tackifiers, conductive additives, flame retardants, ultraviolet (UV) protectors, and the like. These additives may take the form of various geometries including, but are not limited to, particles, flakes, rods, and the like.

Composite Materials

The curable composition as discussed above may be combined with reinforcement fibers to form a composite material or structure. Reinforcing fibers may take the form of whiskers, short fibers, continuous fibers, filaments, tows, bundles, sheets, plies, and combinations thereof. Continuous fibers may further adopt any of unidirectional, multi-directional, non-woven, woven, knitted, stitched, wound, and braided configurations, as well as swirl mat, felt mat, and chopped-fiber mat structures. The composition of the fibers may be varied to achieve the required properties for the final composite structure. Exemplary fiber materials may include, but are not limited to, glass, carbon, graphite, aramid, quartz, polyethylene, polyester, poly-p-phenylene-benzobisoxazole (PBO), boron, polyamide, graphite, silicon carbide, silicon nitride, and combinations thereof.

To form composite materials, the reinforcing fibers are impregnated or infused with the curable composition using conventional processing techniques such as, but not limited to prepregging via resin film impregnation and resin infusion via Resin Transfer Molding (RTM) or Vacuum-Assisted RTM (VaRTM).

Reinforcing fibers may take the form of short fibers, continuous fibers, filaments, tows, bundles, sheets, plies, and combinations thereof. Continuous fibers may further adopt any one of unidirectional, multi-directional, non-woven, woven, knitted, stitched, wound, and braided configurations, as well as swirl mat, felt mat, and chopped-fiber mat structures. The composition of the fibers may be varied to achieve the required properties for the final composite structure. Exemplary fiber materials may include, but are not limited to, glass, carbon, graphite, aramid, quartz, polyethylene, polyester, poly-p-phenylene-benzobisoxazole (PBO), boron, polyamide, graphite, silicon carbide, silicon nitride, and combinations thereof.

To fabricate a composite part from prepregs, plies of impregnated reinforcing fibers are laid up on a shaping tool and laminated together by heat and pressure, for example by autoclave, or vacuum moulding, or by heated rollers, at a temperature above the curing temperature of the resin composition. Upon curing of the matrix resin in the composite materials, composite structural parts can be formed.

To fabricate a composite part through resin infusion, e.g. RTM or VaRTM processes, the first step is to form a dry fiber preform in the shape of the desired structural part. The preform generally includes a number of fabric layers or plies made from dry reinforcement fibers that impart the desired reinforcing properties to a resulting composite part. After the fiber preform has been formed, the preform is placed in a mold. The curable resin composition is injected/infused directly into fiber preform, and then the resin-infused preform is cured.

EXAMPLES

In the Examples below,
HPLC is High Performance Liquid Chromatography,
LCMS is Liquid Chromatography Mass Spectrometry,
GCMS is Gas Chromatography Mass Spectrometry,
HPSEC is High Performance Size Exclusion Chromatography,
NMR is Nuclear Magnetic Resonance Spectroscopy,
DSC is Differential Scanning Calorimetry, and
TLC is Thin Layer Chromatography.

Example 1

Synthesis via Methyl Formcel 81 mL of methyl formcel (1.48 mole) was added to a 4-neck round bottom flask equipped with a reflux condenser, a thermocouple, an overhead stirrer and a nitrogen inlet. 54 g (0.5 mole) of m-toluidine was then added drop-wise to the flask. The solution was then stirred for 2 hrs at room temperature. The disappearance of m-toluidine was observed by TLC.

At this stage, solid 1,1,1-tris (4-hydroxyphenyl)ethane was added in lots. The reaction mixture was then heated to reflux. The reaction was monitored by HPLC, which showed one major product peak. The reaction mixture was cooled and diluted with methylene chloride. The methylene chloride solution was then washed with methanol/water mixture. The methylene chloride layer was dried with $Na_2SO_4$, filtered and the solvent removed under reduced pressure. The residue was treated with methanol to obtain a white solid, which was filtered, washed with methanol, and then dried.

The dried solid of benzoxazine reaction product was analyzed by LCMS and by NMR spectroscopy. The analysis confirmed the presence of m-tris-benzoxazine as the major component.

Figure 1:
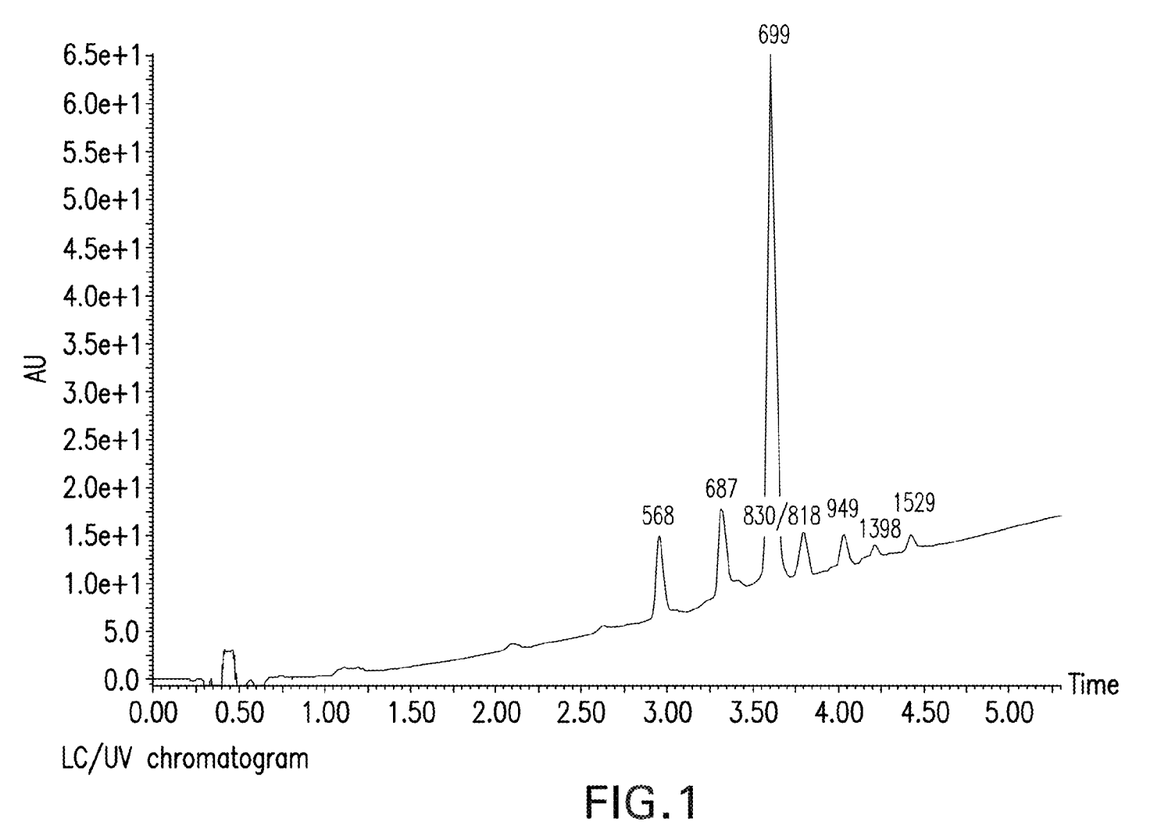
FIG. 1 is a LC/UV chromatogram for a benzoxazine reaction product synthesized according to a first method.

FIG. 1 is a chromatogram for the dried solid of benzoxazine reaction product, showing the major component (MW=699, $C_{47}H_{45}N_3O_3$, 62.4 area %) as a substituted trifunctional benzoxazine compound having tris(phenol)ethane+3 toluidine+6$CH_2O$, minus 6$H_2O$. A significant impurity (MW=687, $C_{46}H_{45}N_3O_3$, 10.5 area %) was found partially due to the decomposition of the major component in the LC system. Several additional impurities were also present. Table 1 provides the findings based on the chromatogram shown in FIG. 1.

TABLE 1

| MW | Proposed Identification | Molecular Formula | Area % |
|---|---|---|---|
| 568 | TPE + 2 toluidine + 4 $CH_2O$, minus 4 $H_2O$ | $C_{38}H_{36}N_2O_3$ | 10.7 |
| 687* | TPE + 3 toluidine + 5 $CH_2O$, minus 5 $H_2O$ | $C_{46}H_{45}N_3O_3$ | 10.5 |
| 699 | TPE + 3 toluidine + 6 $CH_2O$, minus 6 $H_2O$ | $C_{47}H_{45}N_3O_3$ | 62.4 |
| 830** | TPE + 4 toluidine + 8 $CH_2O$, minus 8 $H_2O$ | $C_{56}H_{54}N_4O_3$ | 5.4 |
| 818** | TPE + 4 toluidine + 7 $CH_2O$, minus 7 $H_2O$ | $C_{55}H_{54}N_4O_3$ | |
| 949 | TPE + 5 toluidine + 9 $CH_2O$, minus 9 $H_2O$ | $C_{64}H_{63}N_5O_3$ | 3.4 |
| 1398 | dimer | $C_{94}H_{90}N_6O_6$ | 1.9 |
| 1529 | dimer + toluidine + 2 $CH_2O$, minus 2 $H_2O$ | $C_{103}H_{99}N_7O_6$ | 1.5 |
| | minor unidentified compounds | | 4.2 |

TPE = tris(phenol)ethane
*Some of this peak is due to the decomposition of the major component in the LC system
**MW = 818 and 830 compounds co-elute The NMR spectra of the m-tris-benzoxazine compound produced in Example 1 matched the predicted chemical structure.

Example 2

Synthesis via Paraformaldehyde 16.510 g of m-toluidine (0.154 mol) was added to a 500 ml jar and stirred at room temperature. 15.04 g of 1,1,1-tris (4-hydroxyphenyl)ethane (0.05 mol) and 37.2 g of p-formaldehyde (0.31 mol) were combined and added to the jar over about 20 minutes. The jar was then placed in an oil bath and heated to 70° C. with vigorous stirring for 15 minutes. Around this temperature an exothermic reaction occurred. The oil bath temperature was raised to 85° C. and stirred for 15 minutes. The temperature was then raised to 110° C. and held for 30 minutes. The temperature was then set to 130° C. and once the internal temperature of the resin reached 110° C. a 30-minute timer was started. After 30 minutes has elapsed, the resulting molten mixture was poured onto release paper and allowed to cool. The solid reaction product was then crushed to a fine powder. The powder was washed twice in NaOH solution (700 $cm^3$, 1 $mol \cdot dm^{-3}$) at 70° C. for 30 mins. The solid was washed with 700 $cm^3$ portions of distilled water at 70° C. until the water was pH7. The solid was then filtered and dried in vacuum at 40° C.

Figure 2A:
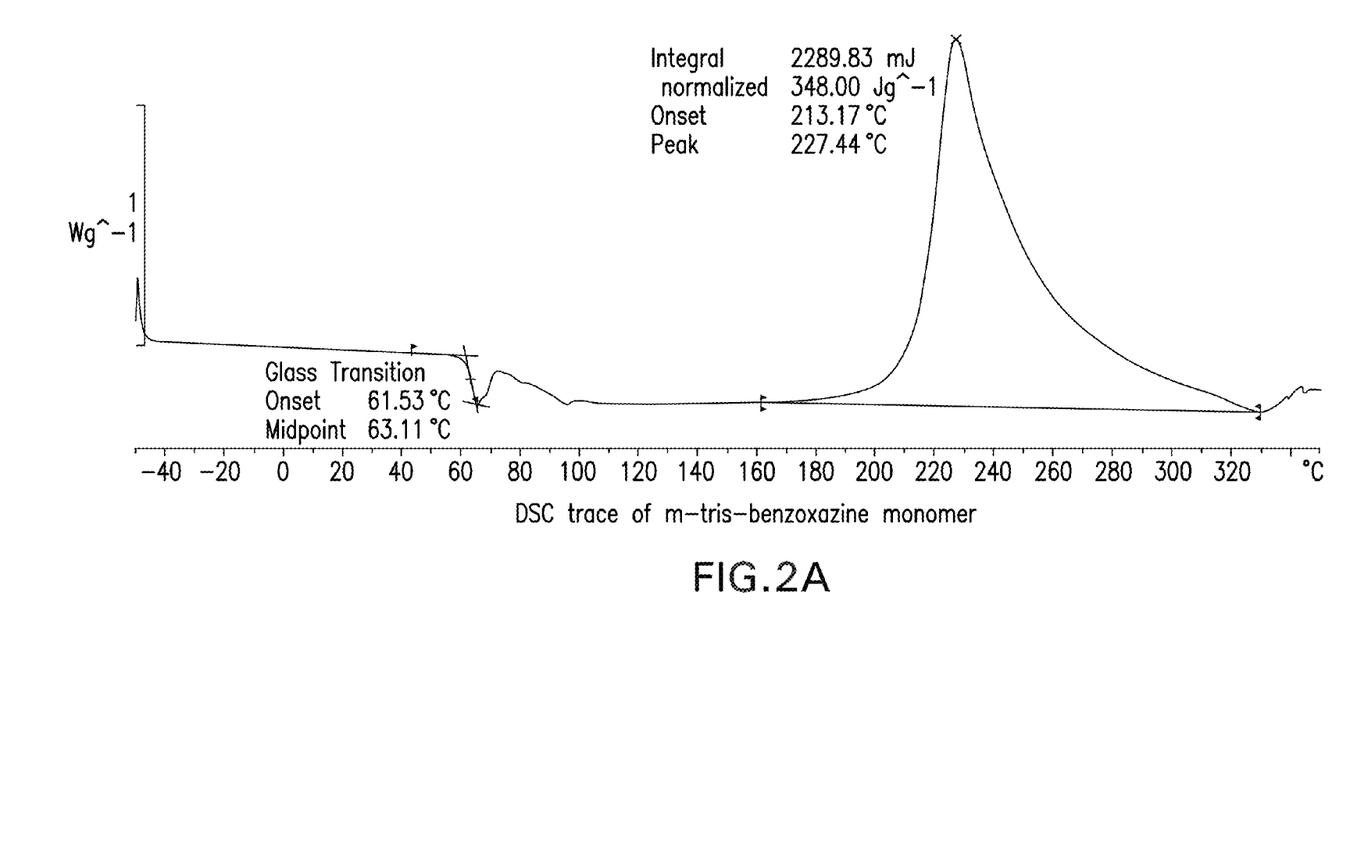
FIG. 2A is the DSC thermogram of a meta-trifunctional benzoxazine with m-toluidine substituents synthesized according to the methods of the present disclosure.
Figure 2B:
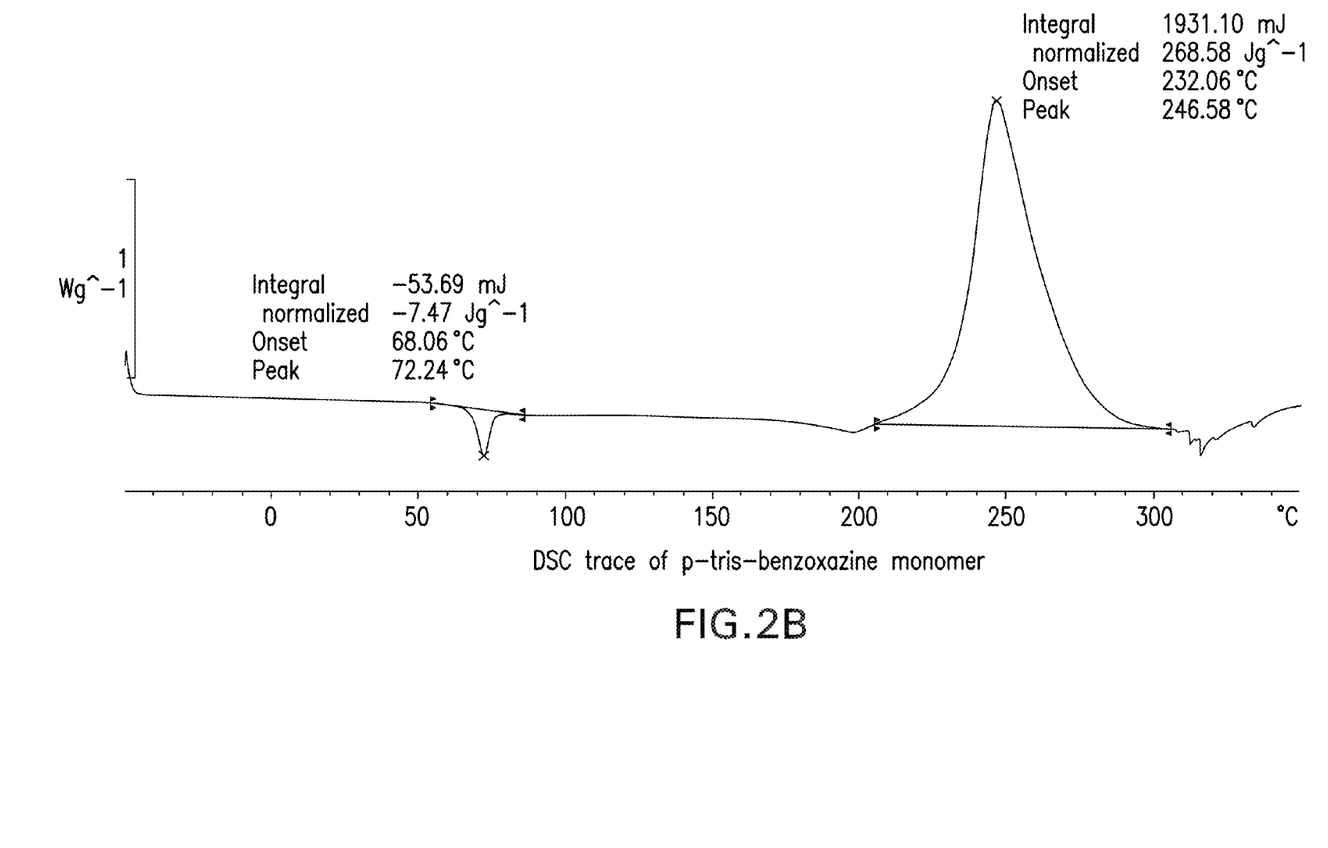
FIG. 2B is the DSC thermogram of a para-trifunctional benzoxazine for comparison.

FIG. 2A is the DSC trace of uncured m-tris benzoxazine produced in this Example. For comparison, the DSC trace of uncured p-tris benzoxazine (Structure II discussed above) is shown in FIG. 2B. As can be seen from these DSC traces, m-tris benzoxazine reacted at a lower temperature than p-tris benzoxazine.

Example 3

A cured, neat resin sample of m-tris benzoxazine was prepared as follows:
1. 10 g-12 g of m-tris benzoxazine was placed in an aluminum dish and degassed in a vacuum oven at 110° C. for 180 minutes.
2. The degassed benzoxazine was then cured in a fan assisted oven using the following standard cure cycle: 25° C. to 180° C. at 1° C. $min^{-1}$, held for 2 hr, 180° C. to 200° C. at 1° C. $min^{-1}$, held for 2 hr, 200° C. to 25° C. at 2° C. $min^{-1}$.

For comparison, a similar sample of p-tris benzoxazine resin was cured under the same cure cycle.

A second sample of m-tris benzoxazine was cured for 2 hr at 180° C. then 2 hr at 200° C., followed by post-curing at 230° C. for 2 hr. A second sample of p-tris benzoxazine was cured for 2 hr at 180° C. then 2 hr at 220° C.

Figure 3:
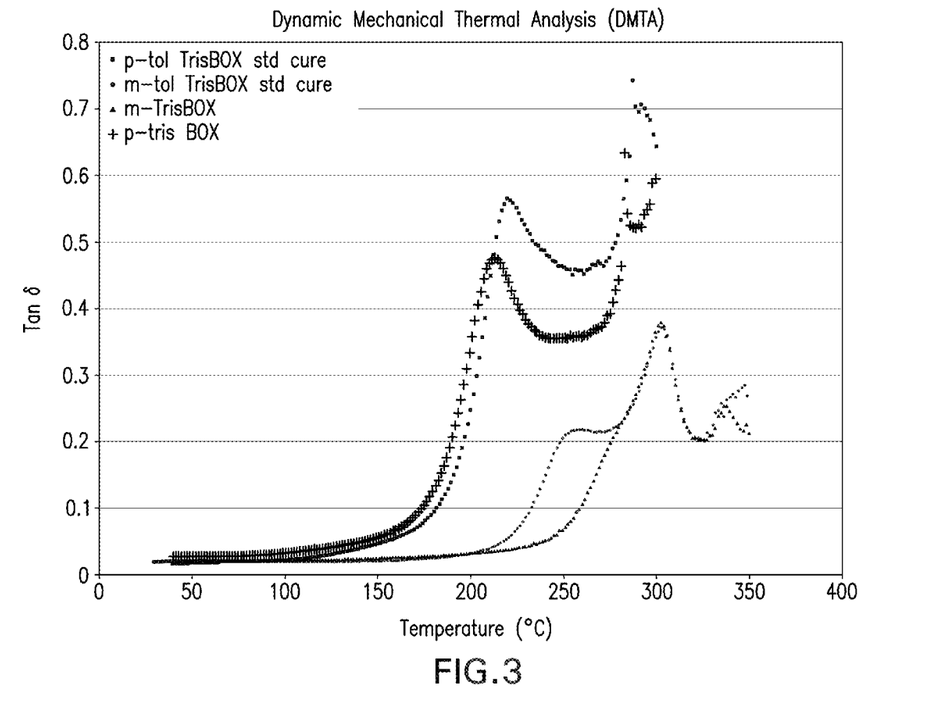
FIG. 3 shows the Dynamic Mechanical Thermal Analysis (DMTA) results for cured samples of meta-trifunctional benzoxazine and para-trifunctional benzoxazine.

FIG. 3 shows the Dynamic Mechanical Thermal Analysis (DMTA) results for the cured benzoxazine samples.

When m-tris benzoxazine was cured under standard conditions (above), a peak in tan delta at ~250° C. was observed. When the same sample was post cured (230° C. for 2 hr), the peak was raised to 300° C.

It was found that raising the heating temperature of the p-tris benzoxazine sample to 220° C. in the final step of the cure cycle did not raise its glass transition temperature ($T_g$), as determined by DMTA. With the cured m-tris benzoxazine sample, a higher temperature post cure did raise the $T_g$. This suggests that higher cure temperatures in the final step of the cure cycle could increase the $T_g$ of the m-tris benzoxazine.

Figure 4A:
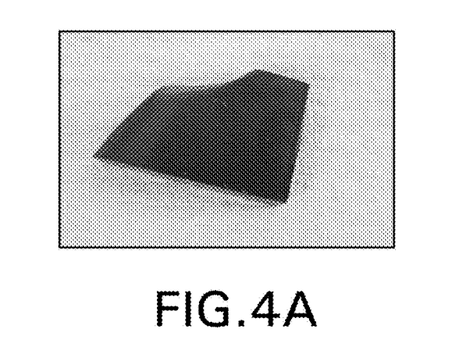
FIGS. 4A and 4B show, respectively, a cured resin sample of meta-trifunctional benzoxazine, and the same cured resin sample after post curing at 230° C. for 2.5 hrs.
Figure 4B:
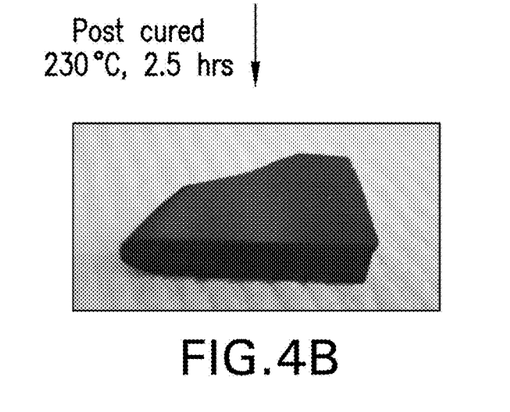

FIG. 4A shows an image of a cured m-tris benzoxazine sample after the standard curing cycle disclosed above, and FIG. 4B shows the same cured sample after post-cure at 230° C. for 2.5 hrs. This result shows that m-tris benzoxazine exhibits thermal stability at high-temperature post cure.

Example 4

Two resin compositions, one with and one without m-tris benzoxazine ("m-Tris-BOX"), were prepared based on the formulations disclosed in Table 2. All values are in weight percentage unless stated otherwise.

TABLE 2

| | Bis-A BOX | Araldite ® CY-179 | m-Tris-BOX | TDP |
|---|---|---|---|---|
| Formulation 1 | 68 | 23 | | 9 |
| Formulation 6 | 47.52 | 22.96 | 20.54 | 8.98 |

Bis-A BOX refers to Bisphenol A benzoxazine. Araldite® CY-179 is a cycloaliphatic epoxy supplied by Huntsman Advanced Materials. TDP refers to thiodiphenol (a catalyst).

A composite laminate was made based on each resin formulation. First, resin films were formed from the resin formulations disclosed in Table 2. Each resin film had a film weight of ~39 gsm (g²/m). Each composite laminate was formed by laying up 24 prepreg plies according to orientation [+45/90/-45/0]3 s. Prepreg was made by placing a layer of unidirectional IM7 carbon fibers between two resin films and using a hot-melt lamination method to impregnate the fibers. The target fabric areal weight (FAW) for the carbon fibers was 145 gsm and 35% resin content per prepreg. Subsequently, the composite laminate was enclosed in a vacuum bag and cured in an autoclave at 8.16 bars for 2 hr at 180° C. and then an additional 2 hr at 200° C.

The cured composite laminates were tested to determine open hole compression (OHC) and open hole tension (OHT) performance using ASTM test methods D6484 and D766 respectively. To obtain data for OHC, 12 in×1.5 in test specimens of cured composite laminates were made. A 0.25 inch hole was drilled in the center of each test specimen. Specimens were conditioned by immersing specimens in a water bath set at 71° C. for 2 weeks. The OHC and OHT results are reported in Tables 3 and 4.

TABLE 3

Open Hole Compression (OHC) Test Values (MPa)

| | Dry (23° C.) | Wet* (82° C.) | Wet* (121° C.) | Wet* (149° C.) |
|---|---|---|---|---|
| Formulation 1 | 349.6 | 322 | 301.3 | 240.6 |
| Formulation 6 | 340.6 | 321.3 | 310.3 | 264.1 |

*conditioned: 2-week water soak

TABLE 4

Open Hole Tension (OHT) Test Values (MPa)

| | Condition | |
|---|---|---|
| Resin | 23° C. | -59° C. |
| Formulation 1 | 483.3 | 473.7 |
| Formulation 6 | 582.6 | 557.1 |

Wet and dry $T_g$ of the cured composite laminates were also determined by Dynamic Mechanical Thermal Analysis (DMTA), and the results are shown in Table 5.

TABLE 5

Composite $T_g$ (° C.) as determined by DMTA

| | Formulation 1 | Formulation 6 |
|---|---|---|
| Dry Tg (E') onset | 208.5 | 231.1 |
| Wet Tg (E') onset | 169.9 | 180.8 |

The composite laminate that contained m-tris benzoxazines yielded better wet OHC performance at higher temperatures, 121° C. and 149° C., as compared to the composite laminate without it. These higher values in wet OHC at 121° C. and 149° C. were also accompanied by a higher OHT value. An increase in dry and wet $T_g$ was also observed for the composite laminate containing m-tris benzoxazine as compared to the composite laminate without it.

What is claimed is:

1. A meta-substituted trifunctional benzoxazine monomer represented by the following structure (A):

(A)

and having a molecular weight (MVV) of about 699 as determined by Liquid Chromatography Mass Spectrometry (LCMS).

2. A reaction product composition obtained by reacting 1,1,1-tris(4-hydroxyphenyl)ethane with m-toluidine and methyl formcel, wherein the composition comprises a meta-substituted trifunctional benzoxazine represented by structure (A) as a major component, and benzoxazines represented by structures (B) and (C) as minor components:

(A)

Major Product: MW 699

(B)

Minor Product: MW 687

(C)

Minor Product: MW 568 and wherein the molecular weight of structure (A), (B) and (C) is 699, 687 and 568, respectively, as determined by Liquid Chromatography Mass Spectrometry (LCMS).

3. The reaction product composition of claim 2, wherein the stoichiometry for reacting 1,1,1-tris(4-hydroxyphenyl)ethane with m-toluidine and methyl formcel is as follows: for each mole of m-toluidine, 0.25-0.5 mole of 1,1,1-tris(4-hydroxyphenyl)ethane, and 1.5-20 moles of methyl formcel.

4. A reaction product composition obtained by preparing a reaction mixture comprising ,1,1-tris(4-hydroxyphenyl)ethane, m-toluidine, and paraformaldehyde; and heating the reaction mixture to a temperature at which chemical reaction occurs, wherein the composition comprises, as a major component, a meta-substituted trifunctional benzoxazine monomer represented by the following structure (A):

(A)

said trifunctional benzoxazine monomer having a molecular weight (MVV) of 699 as determined by Liquid Chromatography Mass Spectrometry (LCMS).

5. A resin composition comprising the meta-substituted trifunctional benzoxazine monomer of claim 1 and another benzoxazine monomer.

6. A resin composition comprising the reaction product of claim 1 and a thermosettable resin.

7. A curable composition comprising:
the meta-substituted trifunctional benzoxazine monomer of claim 1 and at least one thermosettable resin component selected from the group consisting of: monofunctional benzoxazines; multifunctional benzoxazines other than said substituted trifunctional benzoxazine monomer; epoxy resins, bismaleimide (BMI), phenolic resins, formaldehyde-phenol, cyanate ester, unsaturated polyester, and combinations thereof.

8. A curable composition comprising:
the reaction product composition of claim 2 and at least one thermosettable resin component selected from the group consisting of: monofunctional benzoxazines; multifunctional benzoxazines other than said substituted trifunctional benzoxazine monomer; epoxy resins, bismaleimide (BMI), phenolic resins, formaldehyde-phenol, cyanate ester, unsaturated polyester, and combinations thereof.

9. A resin composition comprising:
   the meta-substituted trifunctional benzoxazine monomer of claim 1; and
   a catalyst selected from the group consisting of: boron trifluorodietherate ($BF_3O(Et)_2$); phosphorous pentachloride ($PCl_5$); phosphorous trichloride ($PCl_3$); phosphorus oxychloride ($POCl_3$); titanium chloride ($TiCl_4$); aluminum chloride ($AlCl_3$); antimony pentachloride ($SbCl_5$); thiodiphenol; 2,4-di-tert-butylphenol; methyl tosylate; methyl triflate (MeOTf); cyanate esters; 2-ethyl-4-methylimidazole(EMI); alkylenic acids; adipic acid; p-toluenesulfonic acid; and combinations thereof.

10. The resin composition of claim 5 further comprising a catalyst selected from the group consisting of:
   boron trifluorodietherate ($BF_3O(Et)_2$), phosphorous pentachloride ($PCl_5$), phosphorous trichloride ($PCl_3$), phosphorus oxychloride ($POCl_3$), titanium chloride ($TiCl_4$), aluminum chloride ($AlCl_3$), antimony pentachloride ($SbCl_5$); thiodiphenol; 2,4-di-tert-butylphenol; methyl tosylate; methyl triflate (MeOTf); cyanate esters; 2-ethyl-4-methylimidazole (EMI); alkylenic acids; adipic acid; p-toluenesulfonic acid; and combinations thereof.

11. A composite material comprising reinforcement fibers and a curable matrix resin,
   wherein the curable matrix resin comprises the meta-substituted trifunctional benzoxazine monomer of claim 1.

12. A composite material comprising reinforcement fibers and a curable matrix resin,
   wherein the curable matrix resin comprises the reaction product composition of claim 2.

13. A prepreg comprising a layer of reinforcement fibers impregnated with or embedded in a curable matrix resin comprising the meta-substituted trifunctional benzoxazine monomer of claim 1.

14. The prepreg of claim 13, wherein the reinforcement fibers are in the form of continuous, unidirectionally aligned fibers or woven fabric.

15. The composite materials of claim 11, wherein the reinforcement fibers are selected from carbon fibers, glass fibers, aramid fibers, and combination thereof.

16. A composite structure manufactured by combining reinforcement fibers with the resin composition of claim 5.

17. A composite structure manufactured by combining reinforcement fibers with the resin composition of claim 6.

18. A composite structure manufactured by impregnating or infusing reinforcement fibers with the curable composition of claim 7, followed by curing.

* * * * *